(12) United States Patent
Seifert et al.

(10) Patent No.: US 8,694,128 B2
(45) Date of Patent: Apr. 8, 2014

(54) MEDICAL ELECTRICAL LEAD

(75) Inventors: Kevin R. Seifert, Forest Lake, MN (US); Gregory A. Boser, Richfield, MN (US)

(73) Assignee: Medtronic, Inc., Minneapolis, MN (US)

( * ) Notice: Subject to any disclaimer, the term of this patent is extended or adjusted under 35 U.S.C. 154(b) by 1542 days.

(21) Appl. No.: 12/020,479

(22) Filed: Jan. 25, 2008

(65) Prior Publication Data

US 2009/0192576 A1 Jul. 30, 2009

(51) Int. Cl.
*A61N 1/05* (2006.01)

(52) U.S. Cl.
USPC .......................................... 607/120

(58) Field of Classification Search
USPC .......................................... 607/120
See application file for complete search history.

(56) References Cited

U.S. PATENT DOCUMENTS

| | | | |
|---|---|---|---|
| 3,902,501 A | 9/1975 | Citron et al. | |
| 5,019,090 A * | 5/1991 | Pinchuk | 623/1.15 |
| 5,313,943 A | 5/1994 | Houser et al. | |
| 5,578,068 A | 11/1996 | Laske et al. | |
| 5,645,580 A | 7/1997 | Moaddeb et al. | |
| 5,755,767 A | 5/1998 | Doan et al. | |
| 6,038,482 A | 3/2000 | Vachon | |
| 6,240,321 B1 | 5/2001 | Janke et al. | |
| 6,405,091 B1 * | 6/2002 | Vachon et al. | 607/120 |
| 6,697,676 B2 | 2/2004 | Dahl et al. | |
| 7,177,702 B2 | 2/2007 | Wallace et al. | |
| 7,187,971 B2 * | 3/2007 | Sommer et al. | 607/3 |
| 2004/0068299 A1 | 4/2004 | Laske et al. | |
| 2006/0009830 A1 * | 1/2006 | Atkinson et al. | 607/126 |
| 2006/0036307 A1 | 2/2006 | Zarembo et al. | |

FOREIGN PATENT DOCUMENTS

| | | |
|---|---|---|
| EP | 0622090 | 11/1994 |
| EP | 1462141 | 9/2004 |

OTHER PUBLICATIONS

International Search Report, PCT/US2009/031383, 4 pages.

* cited by examiner

*Primary Examiner* — Joseph Stoklosa (74) *Attorney, Agent, or Firm* — Reed A. Duthler; Carol F. Barry (57) ABSTRACT

A medical device lead is presented. One embodiment of the claimed invention includes a lead body, a conductor, and a flexible component. The lead body includes a proximal end and a distal end. The conductor is coupled to the lead body. A sleeve is coupled to the distal end of the lead body. The flexible component is coupled to the distal end of the sleeve. The distal end of the flexible component includes an outer diameter that is greater than the outer diameter of the proximal end.

22 Claims, 8 Drawing Sheets

MEDICAL ELECTRICAL LEAD

RELATED APPLICATIONS

The present application claims priority and other benefits from U.S. patent application Ser. No. 11/543,284 filed Oct. 13, 2006, the disclosure of which is incorporated herein by reference in its entirety.

TECHNICAL FIELD

The present invention relates to implantable medial devices and, more particularly, to implantable medical leads.

BACKGROUND

Implantable medical devices (IMDs) detect and deliver therapy through a lead. Typically, a stimulation electrode at the distal end of a lead is positioned near or in tissue so that electrical stimuli may be delivered. To reduce or prevent inflammation of the tissue in response to the stimulation electrode, the distal end of the lead includes a monolithic controlled release device that releases an anti-inflammatory agent such as a steroid. It is desirable to develop devices that are able to chronically release anti-inflammatory agents in the vicinity of a stimulation electrode.

BRIEF DESCRIPTION OF DRAWINGS

Aspects and features of the present invention will be appreciated as the same becomes better understood by reference to the following detailed description of the embodiments of the invention when considered in connection with the accompanying drawings, wherein.

DETAILED DESCRIPTION

One embodiment of the present invention is directed to a flexible controlled release device (CRD) that is located at a distal end of a medical electrical lead. The CRD comprises a substantially cylindrical body with a distal end that has an outer diameter greater than the outer diameter at the proximal end. By increasing the outer diameter of the distal end of the CRD, agent elution (e.g., anti-inflammatory drug or agent, anti-arrhythmic agent etc.) of the CRD is increased. Additionally, the larger outer diameter of the distal end of the CRD substantially increases the effective tip area. Effective tip area includes the surface area of the distal end of the CRD and/or the outer diameter of the distal end of the CRD. In effect, the larger outer diameter of the distal end of the CRD allows the diameter of a lead body to be reduced while maintaining or lowering the effective tip pressure. Tip pressure is the amount of force per unit area applied against the distal end of the CRD against an opposing surface such as tissue. The claimed invention has substantially reduced tip pressure by up to 50 percent (%) relative to the smaller sized diameter lead body.

Another embodiment of the claimed invention relates to a flexible component without a steroid. The flexible component comprises a substantially cylindrical body with a distal end that has an outer diameter greater than the outer diameter at the proximal end.

Figure 1:
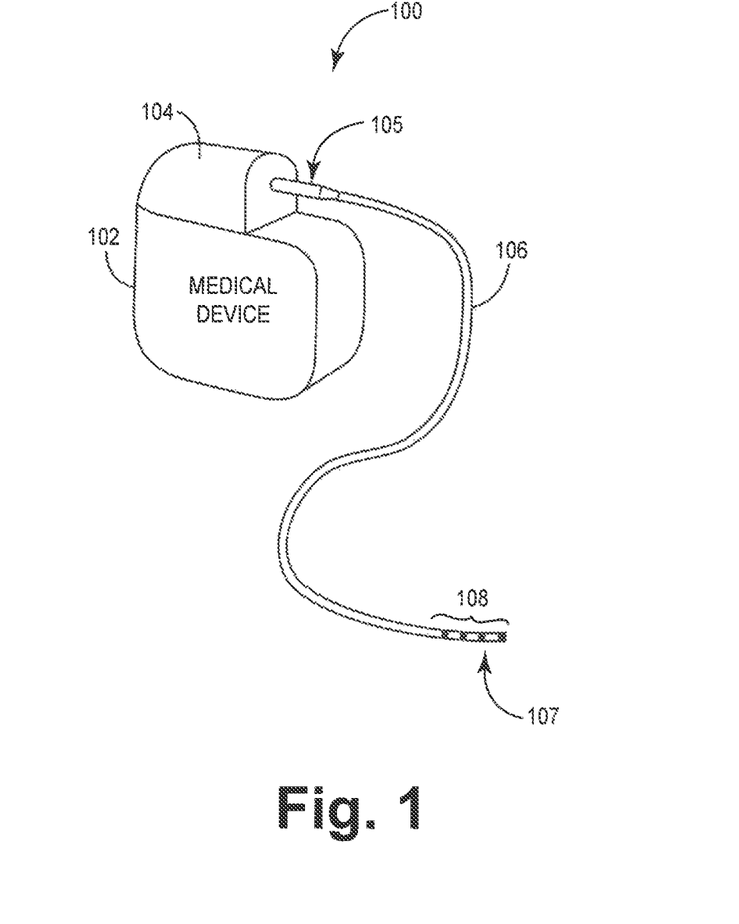
FIG. 1 is a conceptual schematic view of an implantable medical device coupled to a medical electrical lead.

FIG. 1 depicts a medical device system 100. Medical device system 100 includes a medical device housing 102 having a connector module 104 (e g. IS-1, DF-1, IS-4 etc.) that electrically couples various internal electrical components of medical device housing 102 to a proximal end 105 of a medical lead 106. A medical device system 100 may comprise any of a wide variety of medical devices that include one or more medical lead(s) 106 such as pacing and/or defibrillation leads and circuitry coupled to the medical lead(s) 106. An exemplary medical device system 100 may take the form of an implantable cardiac pacemaker, an implantable cardioverter, an implantable defibrillator, an implantable cardiac pacemaker-cardioverter-defibrillator (PCD), a neurostimulator, a sensing lead (e.g. oxygen sensor, pressure sensor, chemical sensors etc.), a tissue or muscle stimulator and/or combinations thereof. Medical device system 100 may deliver, for example, pacing, cardioversion or defibrillation pulses to a patient via electrodes 108 disposed on distal end 107 of one or more lead(s) 106.

Figure 2:
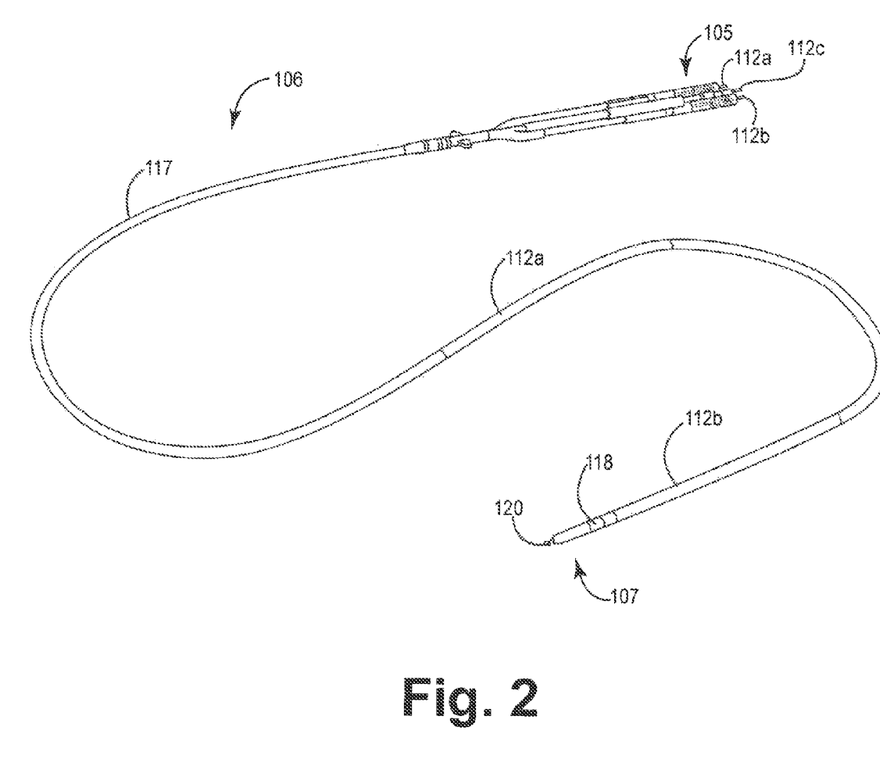
FIG. 2 is a schematic view of a medical electrical lead.

FIG. 2 depicts lead 106 as including an elongated lead body 117 (e.g. pacing and/or defibrillation lead bodies etc.) extending from proximal end 105 to a distal end 107. Lead 106 includes one or more insulated conductive elements 112a-c (coils, wires, coil wound around a filament, cables, conductors etc.) that are directly connected to medical device 100 through connectors (e.g. set screws etc.). One or more conductive elements 112a,b are defibrillation electrodes that extend from proximal end 105 through a portion of lead body 117. Lead 106 also includes a conductive element 112c that extends from the proximal end 105 to ring electrode 118 and another conductive element 112c that extends from proximal end 105 to tip electrode 120.

Figure 3:
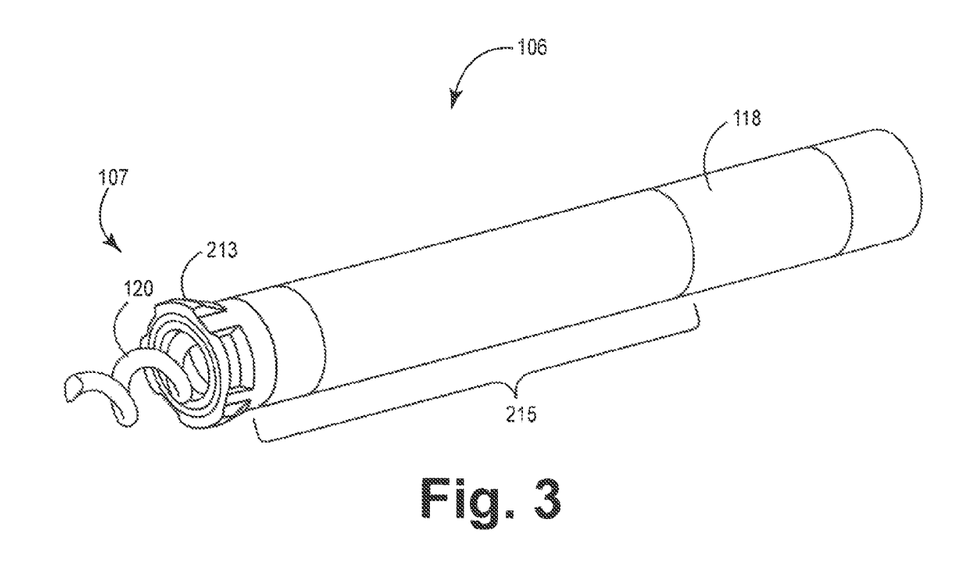
FIG. 3 is a schematic view of an exemplary distal end of the lead depicted in FIG. 2.

FIG. 3 depicts details of a distal end 107 of a medical lead 106. Distal end 107 of a medical lead 106 includes a ring electrode 118, a tip electrode 120, a sleeve member 215 (also referred to as a sleeve head, or sleeve), and a soft distal flexible component 213 that optionally includes an agent (e.g. antiarryhymic, anti-inflammatory etc.). Sleeve member 215 supports deployment of tip electrode 120 and, in one embodiment, separates ring electrode 118 from tip electrode 120. Sharpened distal tip electrode 120, which facilitates fixation of distal end 107 of lead 108 into tissue of a patient, passes through a lumen formed by an inner diameter of flexible component 213. Flexible component 213, depicted in greater detail in FIGS. 4-6, optionally provides chronic agent (e.g., antiarryhymic, anti-inflammatory etc.) elution in the vicinity of tip electrode 120. The agent (e.g., sodium dexamethasone phosphate etc.) enters body fluid and then contacts the tissue adjacent to the helical tip electrode 120.

Figure 8A:
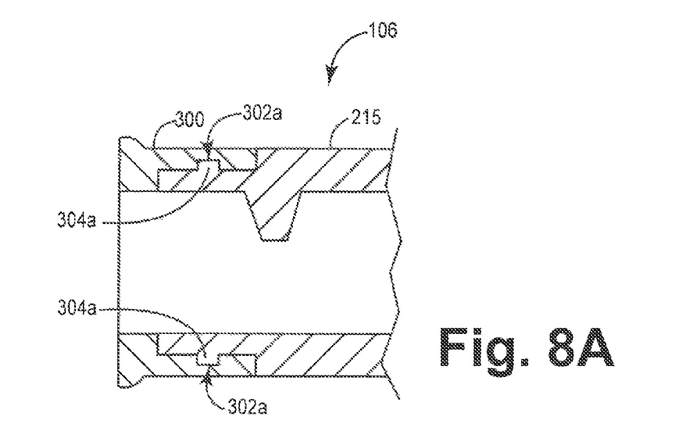
FIG. 8A depicts a schematic cross-sectional view of a flexible component mechanically connected to a sleeve.
Figure 8B:
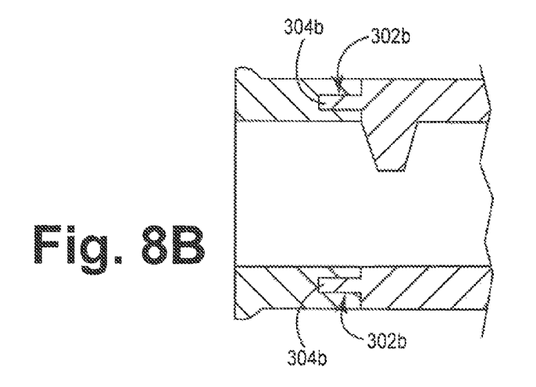
FIG. 8B depicts a schematic cross-sectional view of a flexible component mechanically connected to a sleeve.
Figure 8C:
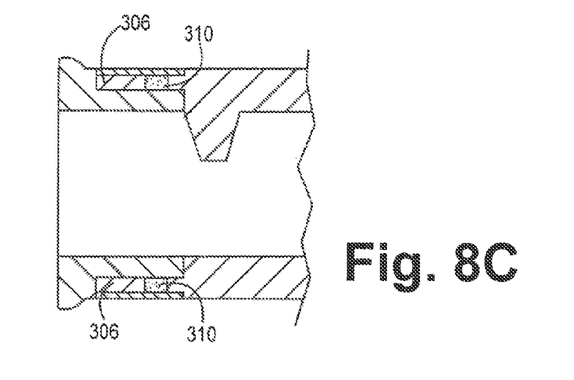
FIG. 8C depicts a schematic cross-sectional view of a flexible component mechanically connected to a sleeve.

Flexible component 213 is directly coupled to sleeve member 215 through mechanical means and/or an adhesive bond. Referring briefly to FIGS. 8A-8C, flexible component 300 is shown to be mechanically connected to sleeve member 215 through one or more grooves 302, formed for a female member while sleeve member 215 includes one or more protruding male member(s). In another embodiment, sleeve member 215 may be configured to include one or more grooves for a male member whereas flexible component 213 would be configured to include corresponding female groove members. Alternatively, the grooves could be located solely in the male member with a recessed region that is configured to receive an adhesive to form an interlock between the male and female members. In still yet another embodiment, the surface of the outer diameter (D2) of proximal end 219 of flexible component 213 is directly connected to sleeve member 215, through, for example, an adhesive bond. Exemplary adhesive bonds include silicone adhesive (e.g. Nusil 1137 commercially available from Nusil located in Carpinteria, Calif. etc) an urethane adhesive, or other suitable adhesives.

Figure 4:
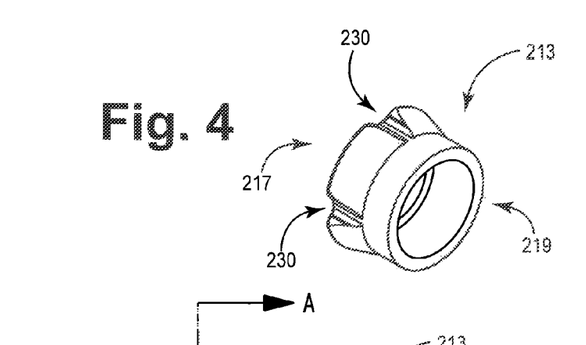
FIG. 4 is a schematic view of a flexible component at the distal end of the lead depicted in FIG. 3.
Figure 5:
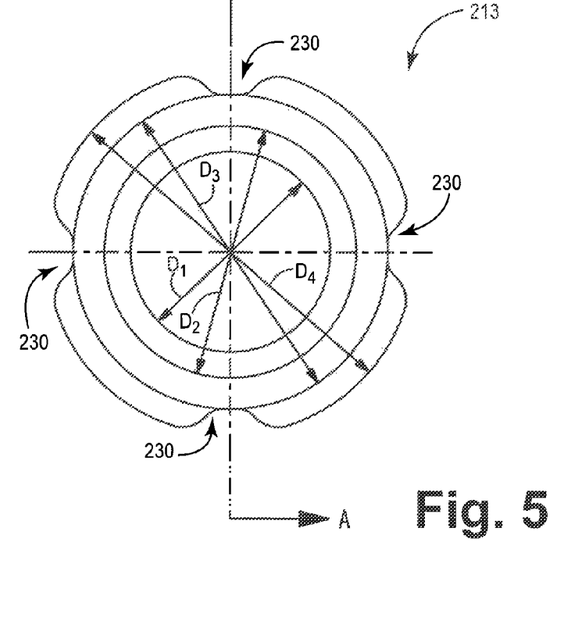
FIG. 5 is a schematic end view of the flexible component depicted in FIG. 4.
Figure 6:
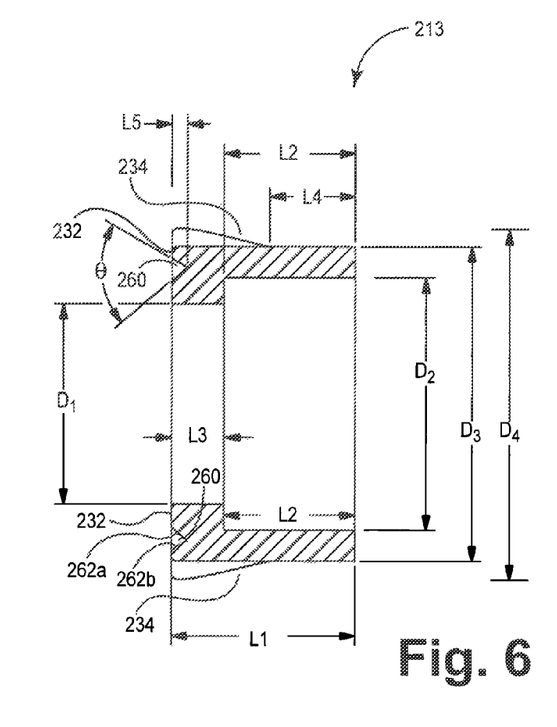
FIG. 6 is a cross-sectional view of the flexible component depicted in FIG. 5.

Flexible component 213 is substantially cylindrical or concentric in shape. Substantially cylindrical is defined as a cylinder within ten percent of the shape of a standard cylinder shape. Flexible component 213 extends a total length of L1 and includes a flared distal end 217 and a proximal end 219 with a lumen therebetween. The stepped inner diameter includes a first inner diameter (D1) that extends a length of about L3 from the distal end 217 and a second inner diameter (D2) that extends a length of about L2. In alternative embodiments, the inner diameter of flexible component 213 may be tapered or straight. Flexible component 213 also includes an outer diameter D3 at the proximal end 219 and outer diameter D4 at the flared distal end 217. Distal end 217 of flexible component 213 begins to flare at a length of L4 from proximal end 219 of flexible component 213. In yet another embodiment, first inner diameter D1 is shifted or offset from second inner diameter D2 to align with entry point of helix 120. In this embodiment the diameter D1 is reduced a near the helix diameter and such that it substantially occludes or covers the distal face 232 of the flexible component 213.

Flexible component 213 includes reinforcing segments 234, one or more recessed regions 230 (also referred to as first recessed regions) along the outer surface (outer diameter D4) of the body of flexible component 213, and recessed regions 230 (also referred to as second recessed regions) along the distal end 217. Reinforcing segments 234 are proximal to surface or distal face 232 and prevent the distal end of flexible component 213 from folding back onto its proximal end. Reinforcing segments 234 may be tapered or rounded to smoothly align with diameter D3.

Optionally, recessed regions 230 are employed to prevent a seal from forming between the outer surface of flexible component 213 and an introducer (not shown) or guide catheter. Specifically, recessed regions 230 allows fluid (e.g. saline solution, air etc.) to pass between the outer surface of flexible component 213 and the inner diameter of an introducer while the introducer is being passed through a lumen of the body. Specifically, recessed regions 230 prevent the distal tip from fully occluding the introducer during advancement of lead 106. While recessed regions 230 are depicted as substantially triangular in shape, other suitable shapes (e.g. substantially cylindrical, rectangular, other shapes that include at least one triangle (e.g. hexagon etc.), nonshapes etc.) may also be used.

Recessed regions 260 are located along an end surface 232 of outer diameter D4 of flexible component 213. Recessed regions 260 increase the flexibility of flexible component 213. For example, the sides 262a,b of recessed regions 260 are closer together when flexible component 213 is in the introducer. However, once flexible component 213 passes through the introducer, the sides 262a,b of recessed regions 260 are further apart from one another. Accordingly, recessed regions 260 adds flexibility to component 213 that more easily allows component 213 to compress in an introducer as component 213 passes through the introducer and then expands after flexible component 213 exits the distal end of the introducer. Exemplary recessed region 260 may be substantially triangular in shape in which angle θ is formed by a first and second side 260 and having a depth of about L5 from end surface 232. While recessed regions 260 are depicted as substantially triangular in shape, other suitable shapes (e.g., substantially cylindrical, rectangular etc.) may also be used.

Component 213 is flexible such that distal end 217 is able to contract or expand. Flexibility of component 213 may be due, at least in part, to component 213 being comprised of a polymer. Exemplary polymers include silicone (e.g. silastic MDX4-4210, silastic ETR, Q7-4735 and/or Q7-4765 commercially available from Dow Corning located in Midland, Mich.), polyurethane, polyurea, and/or polyurethane-polyurea, polyurethane/silicone blends etc.). The polymer may be molded or formed into its depicted shape through conventional techniques.

Figure 7A:
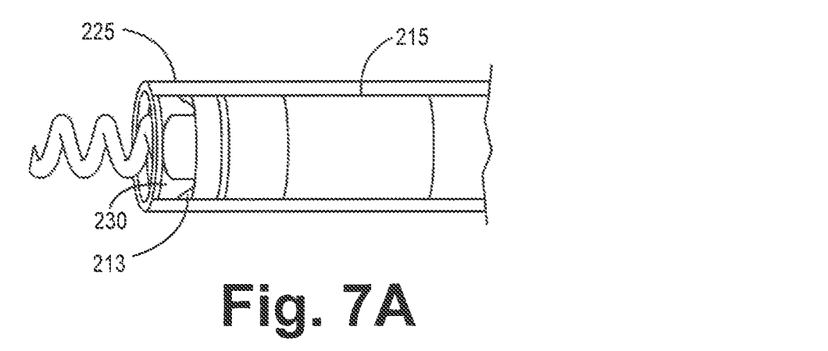
FIG. 7A depicts a schematic side view of a distal end of a lead in which the flexible component is compressed inside a lumen of an introducer before the lead is extended out of the introducer and placed near targeted tissue of a patient.
Figure 7B:
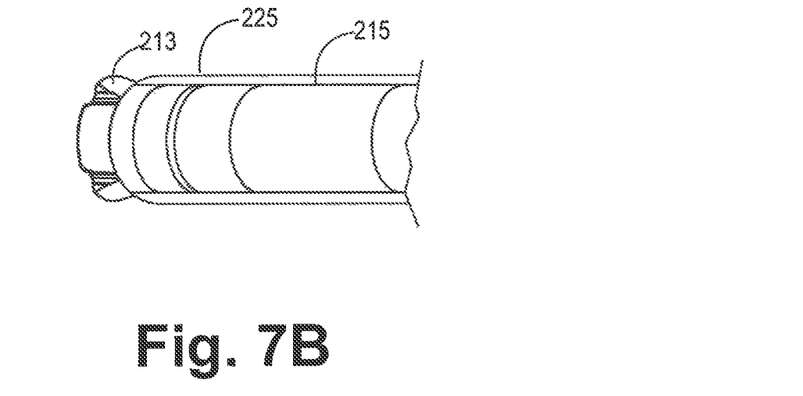
FIG. 7B depicts the flexible component of FIG. 7A that expands after extending in a distal direction away from the distal end of the introducer.
Figure 7C:
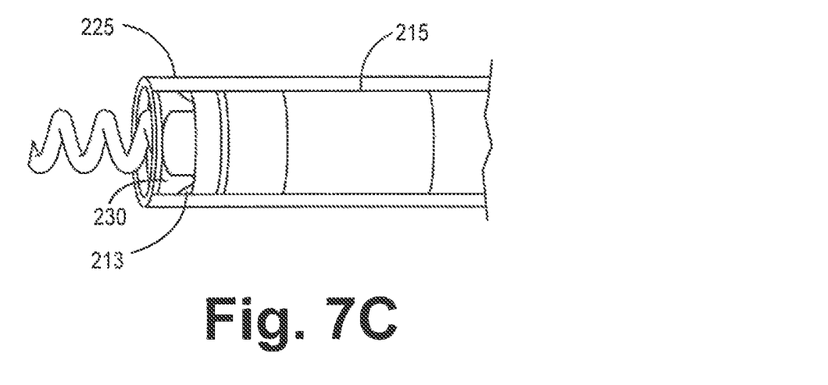
FIG. 7C depicts a distal end of the lead depicted in FIG. 7B in which the CRD is compressed inside a lumen of an introducer after the lead is being repositioned or removed from a body lumen of a patient.

FIGS. 7A-7C depicts flexible component 213 moving from a contracted to expanded positions. Flexible component 213 is initially in a contracted position (FIG. 7A) while disposed in a lumen formed by the inner walls of an introducer 225. Flexible component 213 fully expands (FIG. 7B) once component 213 passes through introducer 225. The physician passes component 213 through the introducer once lead 106 is properly positioned in a patient's tissue. FIG. 7C depicts flexible component 213 in a contracted position after the physician causes component 213 to move in a proximal direction 105 of lead 106.

Table 1 lists exemplary dimensions for one embodiment of flexible component 213; however, other dimensions may be used to create flexible component 213. For D4, a 0.060 inch diameter lead body typically could have a range of about 0.065 inches (5 French) to about 0.080 inches (6.2 French).

TABLE 1

Exemplary dimensions for the flexible component

| Element | Dimension (inches) |
|---|---|
| D1 | 0.038 |
| D2 | 0.048 |
| D3 | 0.060 |
| D4 | 0.070 |
| L1 | 0.035 |
| L2 | 0.025 |
| L3 | 0.010 |
| L4 | 0.016 |
| L5 | 0.000-0.005 |

Table 2 relates to numerous embodiments in which the outer diameter at the distal end 217 is greater than the proximal end 219 of the flexible component 213. For example, the first embodiment includes flexible component 213 in which the outer diameter at the distal end is 3% or greater than the outer diameter at the proximal end for flexible component 213. Depending on the lead body size or outer diameter at the proximal end 219, the introduction size for which lead 106 is targeted and the targeted interference of distal diameter with introducer, flexible component 213 can have many embodiments that increase the effective distal diameter of the flexible component 213. For example, effective distal diameter of the flexible component 213 can increase from about 10% to about 50%.

TABLE 2 embodiments of flexible component

| Embodiment | The outer diameter at the distal end is greater than the outer diameter at the proximal end for the flexible component | The range that the outer diameter at the distal end is greater than the outer diameter at the proximal end for the flexible component |
|---|---|---|
| 1 | 3% | 3% or more |
| 2 | 4% | 4% or more |
| 3 | 5% | 5% or more |
| 4 | 10% | 10% or more |
| 5 | 15% | 15% or more |
| 6 | 20% | 20% or more |
| 7 | 25% | 25% or more |
| 8 | 30% | 30% or more |
| 9 | 35% | 35% or more |
| 10 | 40% | 40% or more |
| 11 | 45% | 45% or more |
| 12 | 50% | 50% or more |

As described, the flexible softer distal tip 217 of flexible component 213 helps to prevent a physician from inadvertently puncturing non-targeted tissue. The distal tip 217 can be enlarged but still be compatible with an introducer. The softer flared distal end of flexible component 213 opens and becomes larger when pressed against an object (i.e. tissue). Additionally, as shown in the Table 1 embodiment, the flared distal end 217 increases the overall tip outer diameter from about 0.060 to an upper limit of about 0.065-0.080 inches, which decreases the lead tip pressure by about 14% to about 38% compared to conventional CRDs for a lead.

Figure 9:
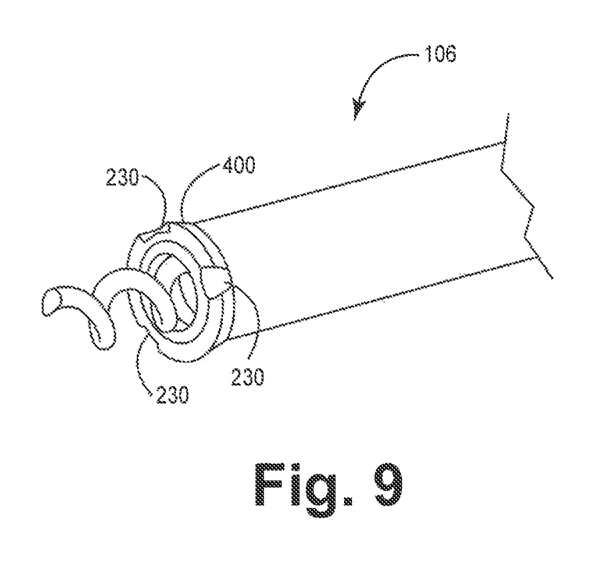
FIG. 9 is a schematic view of another flexible component in the shape of a flange.

Alternative embodiments may also be used to implement the claimed invention. For example, the CRD or nonCRD component can be molded into outer tubing/insulation via reflowing or other tipping operations, as described in U.S. Pat. No. 4,904,433 issued to Williamitis on Feb. 27, 1990. In one embodiment, flexible component 213 and sleeve 215 is formed as a single piece. Molding flexible component 213 onto sleeve 215 is one way of forming flexible component 213 and sleeve 215 as a single piece. In another embodiment, an outer diameter of flexible component 213 lacks the recessed regions 230 depicted in FIGS. 4-6. In still yet another embodiment, FIG. 9 depicts a flanged flexible component with one or more recessed regions alongside an elongated portion of the flange. In the embodiment depicted in FIG. 9, the flanged distal portion of the flexible component can be geometrically incorporated directly into the outer tubing and/or insulation of lead 106. For example, the flange can be molded into the sleeve or outer lead body tubing. In other embodiments, the principles described herein apply to all sizes of leads. For example, the claimed CRD or nonCRD component can be used in a 11 French sized lead or less. Exemplary sized French sized leads include 2, 2.6, 3.5, 4, 4.5, 4.6, 5, 6 etc. While exemplary values are provided for the CRD dimensions, other numerical values may also be used.

Figure 10:
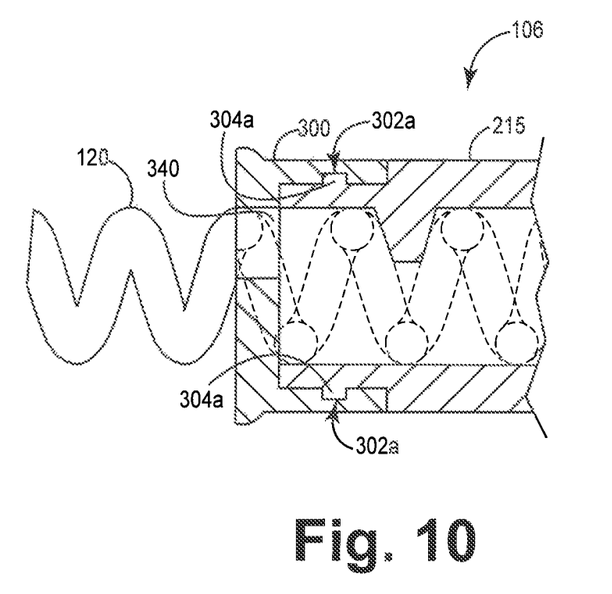
FIG. 10 depicts a schematic cross-sectional view of a helical tip electrode passing through the flexible component.

In one embodiment, as depicted in FIG. 10, a fixation mechanism such as a helical tip electrode passes through the flexible component. As shown, the distal face of the flexible component substantially covers the opening 340 on the face of the flexible component. Any such hole or opening 340 is sized and offset to allow translation or movement of the fixation mechanism. Specifically, the fixation mechanism is allowed to translate and rotate through the hole. In still yet another embodiment, the helix is fixed such that no movement or translation is required. In yet another embodiment, the principles described herein also apply to leads configured for passive fixation such as leads without a helix tip.

The description of the invention is merely exemplary in nature and, thus, variations that do not depart from the gist of the invention are intended to be within the scope of the invention. Such variations are not to be regarded as a departure from the spirit and scope of the invention.

The invention claimed is:

1. A medical device comprising:
   an implantable medical electrical lead that comprises:
   (a) an insulative lead body that includes a proximal end and a distal end;
   (b) at least one conductor disposed in the lead body; and
   (c) a flexible CRD component that includes a proximal end and a flared distal end, the proximal end of the flexible component is coupled to the distal end of the lead body, the distal end of the flexible component includes an outer diameter that is at least 10% greater than the outer diameter of the proximal end of the flexible component;
   an introducer coupled to the lead,
   wherein the distal end of the flexible component flexibly expands once the flexible component extends beyond a distal end of the introducer.

2. The device of claim 1 wherein the flexible component outer diameter at the distal end is 10 percent (%) or greater than the outer diameter at the proximal end of the flexible component.

3. The device of claim 1 wherein the flexible component outer diameter of the distal end is 20% or greater than the outer diameter of the proximal end of the flexible component.

4. The device of claim 1 wherein the flexible component outer diameter of the distal end is 30% or greater than the outer diameter of the proximal end of the flexible component.

5. The device of claim 1 wherein the flexible component includes an inner surface and an outer surface, one or more recessed regions are disposed in the outer surface of the flexible component.

6. The device of claim 5 wherein the one or more recessed regions disposed in the outer surface of the flexible component prevents occluding of the introducer during advancement of the lead through a body lumen.

7. The device of claim 1 wherein the distal end of the flexible component is flared.

8. The device of claim 1 wherein the flared distal end of the flexible component has an outer diameter that is greater than the proximal end of the flexible component by about 10 to 35%.

9. The device of claim 1 wherein the flexible component includes at least one reinforcing segment.

10. The lead according to claim 1 wherein the flexible component comprises one of a silicone, polyurethane, polyurea, polyurethane-polyurea, and polyurethane-silicone.

11. A device according to claim 1 wherein the flexible component is in a contracted position when within the introducer.

12. A device according to claim 1 wherein the flexible component is in a interference fit when within the introducer.

13. A device according to claim 1 wherein the flared distal end displays a taper.

14. A device according to claim 1 wherein the flared distal end comprises a flange having an outer diameter that is at least 10% greater than the outer diameter of the proximal end of the flexible component.

15. A device according to claim 1 wherein the flexible CRD component comprises a steroid, releasable from the component.

16. A device according to claim 1 wherein the flexible CRD component comprises an anti-inflamatory agent releasable from the component.

17. A device according to claim 1 wherein the flexible CRD component comprises an anti-arrhythmic agent, releasable from the component.

18. A device according to claim 1 further comprising an electrode coupled to the conductor.

19. A device according to claim 15 wherein the electrode comprises a helical electrode extending distal to the flexible CRD component.

20. A device according to claim 15 wherein the electrode comprises a helical electrode extendable distal to the flexible CRD component.

21. A medical device comprising:
   an implantable medical electrical lead that comprises:
      (a) an insulative lead body that includes a proximal end and a distal end;
      (b) at least one conductor disposed in the lead body; and
      (c) a flexible CRD component that includes a proximal end and a distal end, the proximal end of the flexible component is coupled to the distal end of the lead body and the distal end of the flexible component includes an outer diameter that is at least 10% greater than the outer diameter of the lead body;
   an introducer coupled to the lead,
   wherein the distal end of the flexible component flexibly expands once the flexible component extends beyond a distal end of the introducer.

22. A medical device comprising:
   an implantable medical electrical lead that comprises:
      (a) an insulative lead body that includes a proximal end and a distal end;
      (b) at least one conductor disposed in the lead body; and
      (c) a flexible CRD component that includes a proximal end and a distal end, the proximal end of the flexible component is coupled to the distal end of the lead body and the distal end of the flexible component includes an outer diameter that is at least 10% greater than the proximal end;
   an introducer coupled to the lead,
   wherein the distal end of the flexible component flexibly expands once the flexible component extends beyond a distal end of the introducer.

\* \* \* \* \*